(12) United States Patent
Amirrashedi et al.

(10) Patent No.: US 11,172,906 B2
(45) Date of Patent: Nov. 16, 2021

(54) NORMALIZATION OF A POSITRON EMISSION TOMOGRAPHY SCANNER

(71) Applicants: Mahsa Amirrashedi, Tehran (IR); Mohammad reza Ay, Tehran (IR); Saeed Sarkar, Tehran (IR); Mohammad Hossein Farahani, Tehran (IR)

(72) Inventors: Mahsa Amirrashedi, Tehran (IR); Mohammad reza Ay, Tehran (IR); Saeed Sarkar, Tehran (IR); Mohammad Hossein Farahani, Tehran (IR)

(73) Assignee: PARTO NEGAR PERSIA (PNP) COMPANY, Tehran (IR)

(*) Notice: Subject to any disclaimer, the term of this patent is extended or adjusted under 35 U.S.C. 154(b) by 121 days.

(21) Appl. No.: 16/746,447

(22) Filed: Jan. 17, 2020

(65) Prior Publication Data

US 2020/0146649 A1 May 14, 2020

Related U.S. Application Data

(60) Provisional application No. 62/793,895, filed on Jan. 18, 2019.

(51) Int. Cl.
*A61B 6/00* (2006.01)
*G01N 23/22* (2018.01)
(Continued)

(52) U.S. Cl.
CPC .............. *A61B 6/583* (2013.01); *A61B 6/037* (2013.01); *A61B 6/5258* (2013.01);
(Continued)

(58) Field of Classification Search
CPC ..... A61B 6/583; A61B 6/5258; A61B 6/5282; A61B 6/037; G01T 1/2985; G01T 1/1647;
(Continued)

(56) References Cited

U.S. PATENT DOCUMENTS

2019/0313993 A1* 10/2019 Zhou ...................... A61B 6/502

FOREIGN PATENT DOCUMENTS

WO WO-2020228587 A1 * 11/2020 ............. A61B 6/037

* cited by examiner

*Primary Examiner* — Michael C Bryant
(74) *Attorney, Agent, or Firm* — Bajwa IP Law Firm; Haris Zaheer Bajwa

(57) ABSTRACT

A method for normalization of a positron emission tomography (PET) scanner. The PET scanner includes a plurality of blocks. Each of the plurality of blocks includes a plurality of rows. Each of the plurality of rows includes a plurality of actual detectors and an unused area. The method includes acquiring a plurality of lines of response (LORs) by scanning a normalization phantom, obtaining a plurality of actual counts by extracting a plurality of LORs subsets from the plurality of LORs and counting a number of elements in each LORs subset, generating a plurality of virtual detectors in each of the plurality of rows by assigning the unused area to the plurality of virtual detectors, generating a count profile for the plurality of actual detectors, estimating a plurality of virtual counts based on the count profile, and applying a normalization process on the plurality of blocks.

19 Claims, 13 Drawing Sheets

(51) Int. Cl.
*A61B 6/03* (2006.01)
*G06T 11/00* (2006.01)
*G01T 1/29* (2006.01)
*G01T 1/164* (2006.01)

(52) U.S. Cl.
CPC .......... *A61B 6/5282* (2013.01); *G01N 23/22* (2013.01); *G01T 1/1647* (2013.01); *G01T 1/1648* (2013.01); *G01T 1/2985* (2013.01); *G06T 11/005* (2013.01); *G01N 2223/108* (2013.01); *G01N 2223/419* (2013.01); *G06T 2210/41* (2013.01)

(58) Field of Classification Search
CPC ..... G01T 1/1648; G06T 11/005; G01N 23/22; G01N 23/046; G01N 2223/108; G01N 2223/419

See application file for complete search history.

ized scintillation crystals may be applied. Such pixelated crystals may be optically coupled with an array of photocathodes. Interaction of gamma photons with a scintillator produces lines of response (LORs) that include light photons. The light photons are then converted to electrons by interacting with the photocathode after they pass through the scintillator crystal.

Systematic differences in intrinsic detector efficiencies and geometrical properties of PET scanners may lead to variations among different LORs which may increase bias and decrease uniformity in reconstructed images. To overcome this issue, different normalization techniques have been introduced to compensate variations among different LORs by reducing variation effects on overall performance of PET scanners. However, non-negligible gaps between different detectors in a PET scanner may lead to a lack of data that may be required for acceptable normalization.

There is, therefore, a need for a method that provides appropriate data for gaps between detectors in PET scanners. There is further a need for a normalization approach that may reduce image non-uniformity caused by gaps between detectors in PET scanners.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for normalization of a positron emission tomography (PET) scanner. An exemplary PET scanner may include a plurality of blocks. Each of the plurality of blocks may include a plurality of rows. Each of the plurality of rows may include a plurality of actual detectors and an unused area. An exemplary unused area may include a respective region in each of the plurality of rows. An exemplary respective region may exclude the plurality of actual detectors.

An exemplary method may include acquiring a plurality of lines of response (LORs) by scanning a normalization phantom utilizing the PET scanner, obtaining a plurality of actual counts by extracting a plurality of LORs subsets from the plurality of LORs and counting a number of elements in each LORs subset of the plurality of LORs subsets, generating a plurality of virtual detectors in each of the plurality of rows by assigning the unused area to the plurality of virtual detectors, generating a count profile for the plurality of actual detectors, estimating a plurality of virtual counts based on the count profile, and applying a normalization process on the plurality of blocks based on the plurality of actual counts and the plurality of virtual counts. An exemplary normalization phantom may include a homogenous cylindrical phantom.

In an exemplary embodiment, each respective LOR of the plurality of LORs may be associated with an actual detector of the plurality of actual detectors. In an exemplary embodiment, each of the plurality of LORs subsets may be associated with a respective actual detector of the plurality of actual detectors. In an exemplary embodiment, the count profile may be associated with the plurality of actual counts. An exemplary plurality of virtual counts may be associated with the plurality of virtual detectors.

In an exemplary embodiment, assigning the unused area to the plurality of virtual detectors may include calculating a total number of detectors in a row of the plurality of rows, calculating a number of virtual detectors in the row, dividing the unused area to a plurality of segments, and assigning each of the plurality of segments to a respective virtual detector of the plurality of virtual detectors. In an exemplary embodiment, a number of the plurality of segments may be equal to the number of the plurality of virtual detectors.

In an exemplary embodiment, generating the count profile may include fitting a curve to variations of the plurality of actual counts with respect to a plurality of actual positions. In an exemplary embodiment, each of the plurality of actual positions may be associated with a respective actual detector of the plurality of actual detectors.

In an exemplary embodiment, estimating the plurality of virtual counts may include estimating each of the plurality of virtual counts by extracting a respective value from the curve. An exemplary respective value may correspond to a respective virtual position of a plurality of virtual positions. In an exemplary embodiment, each of the plurality of virtual positions may be associated with a respective virtual detector of the plurality of virtual detectors.

In an exemplary embodiment, applying the normalization process may include generating a plurality of complex detectors by integrating the plurality of actual detectors and the plurality of virtual detectors, generating a plurality of complex positions by integrating the plurality of actual detectors and the plurality of virtual positions, and applying a component-based normalization process on the plurality of complex detectors. In an exemplary embodiment, each of the plurality of complex positions may be associated with a respective complex detector of the plurality of complex detectors.

Other exemplary systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary method and system for normalization of a positron emission tomography (PET) scanner. An exemplary method may introduce virtual detectors in gaps between actual detectors in a detectors block of a PET scanner. An exemplary count profile may then be obtained for the actual detectors of the PET scanner by scanning a normalization phantom and counting a number of photons that interact with each detector. Based on the count profile, a virtual count may be estimated for each virtual detector. As a result, all the gaps may be replaced with new detectors with the determined number of counts. A normalization technique may then be applied on the new set of detectors (including actual and virtual detectors) based on the obtained counts for each of the detectors. Consequently, image non-uniformity may be significantly reduced due to replacing missing data of gaps in detector blocks with appropriate data. An exemplary normalization technique may be followed by any conventional analytical (such as filtered-back-projection) or iterative reconstruction method. An exemplary processor may be utilized for a real-time implementation of different steps of the exemplary method, without a need for manually operating the PET scanner.

Figure 1A:
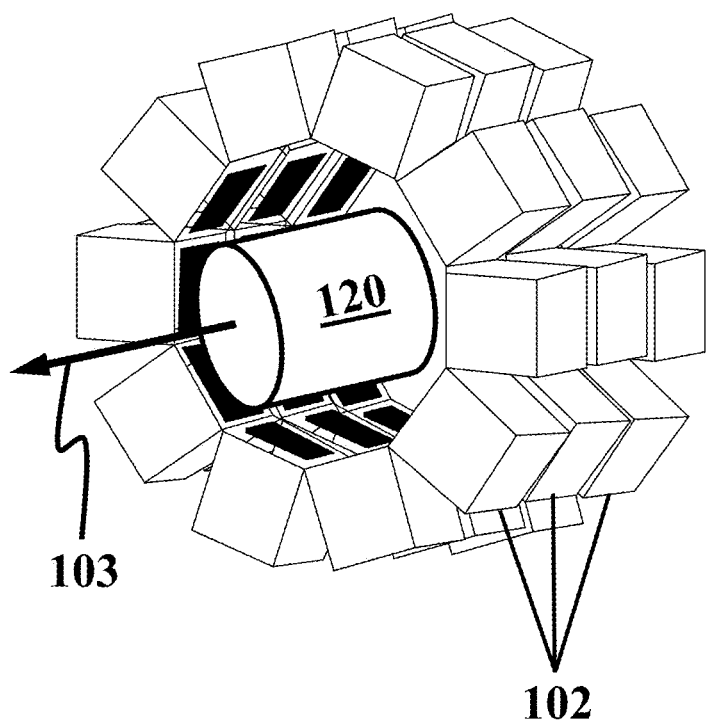
FIG. 1A shows a schematic of a positron emission tomography (PET) system, consistent with one or more exemplary embodiments of the present disclosure.

FIG. 1A shows a schematic of a PET scanner, consistent with one or more exemplary embodiments of the present disclosure. An exemplary PET scanner 100 may include a plurality of block rings 102. In an exemplary embodiment, plurality of block rings 102 may be arranged in an axial direction 103.

Figure 1B:
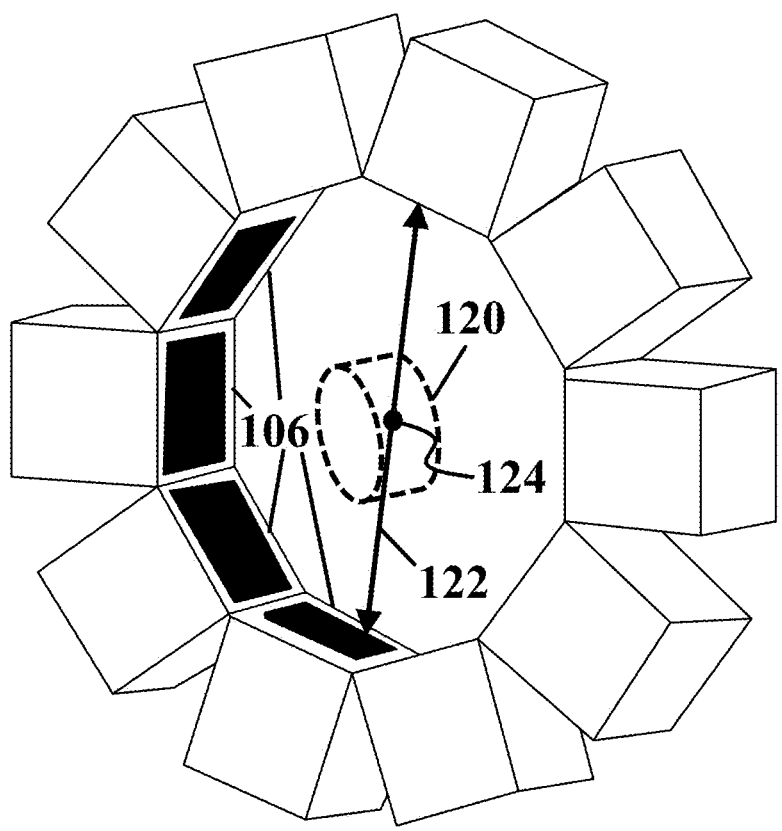
FIG. 1B shows a schematic of a block ring, consistent with one or more exemplary embodiments of the present disclosure.

FIG. 1B shows a schematic of a block ring, consistent with one or more exemplary embodiments of the present disclosure. An exemplary block ring 104 of plurality of block rings 102 may include a plurality of blocks 106 (represented by four exemplary blocks in FIG. 1B).

Figure 1C:
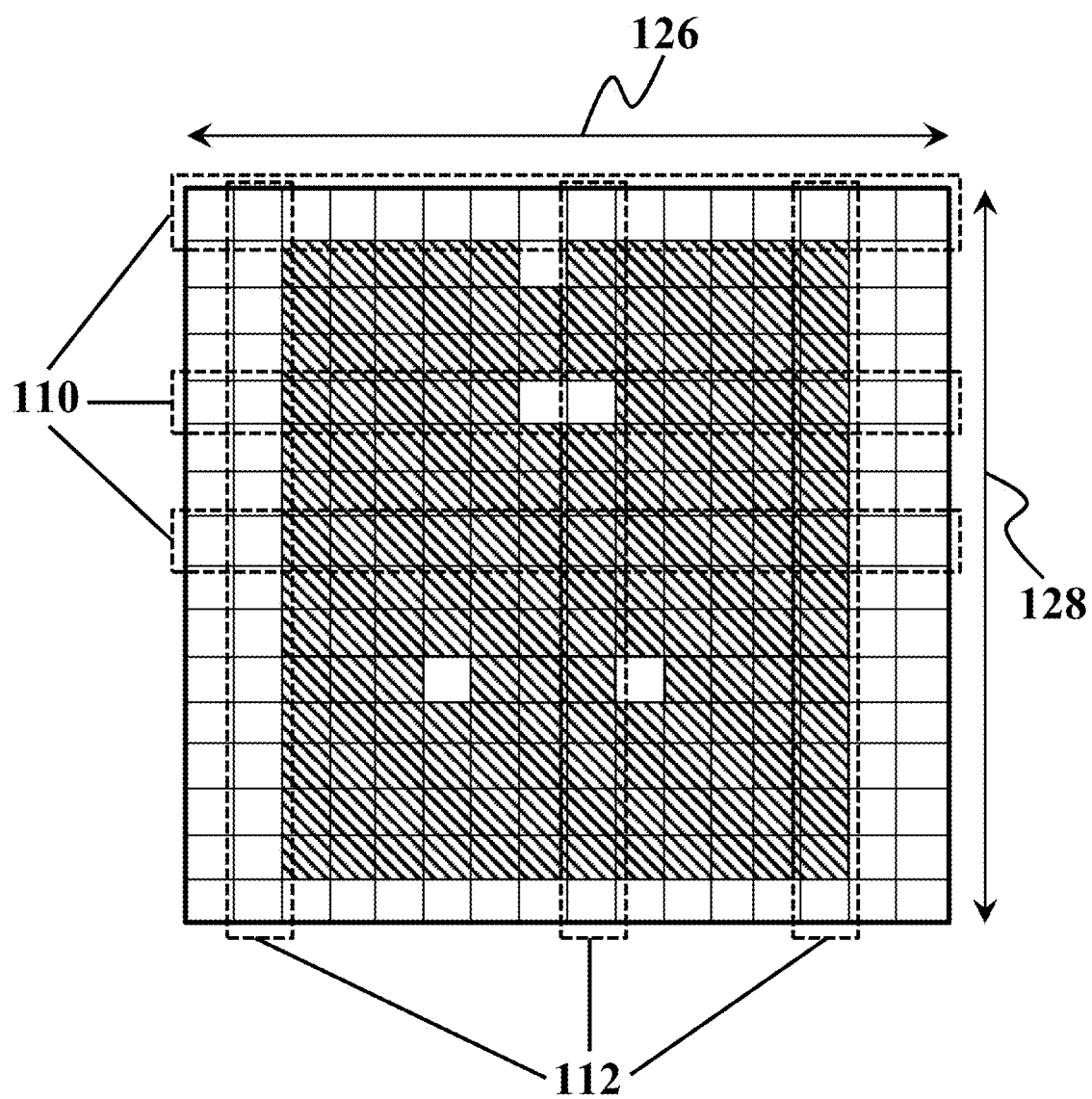
FIG. 1C shows a schematic of a front view of a block, consistent with one or more exemplary embodiments of the present disclosure.

FIG. 1C shows a schematic of a front view of a block, consistent with one or more exemplary embodiments of the present disclosure. An exemplary block 108 of the plurality of plurality of blocks 106 may include a plurality of rows. In an exemplary embodiment, the plurality of rows may include a plurality of transaxial rows 110 (represented by three exemplary transaxial rows in FIG. 1C). Referring again to FIG. 1A, in an exemplary embodiment, a direction of each of plurality of transaxial rows 110 may be perpendicular to axial direction 103. In an exemplary embodiment, the plurality of rows may include a plurality of axial rows 112 (represented by three exemplary axial rows in FIG. 1C). In an exemplary embodiment, a direction of each of plurality of axial rows 112 may be parallel to axial direction 103.

Figure 1D:
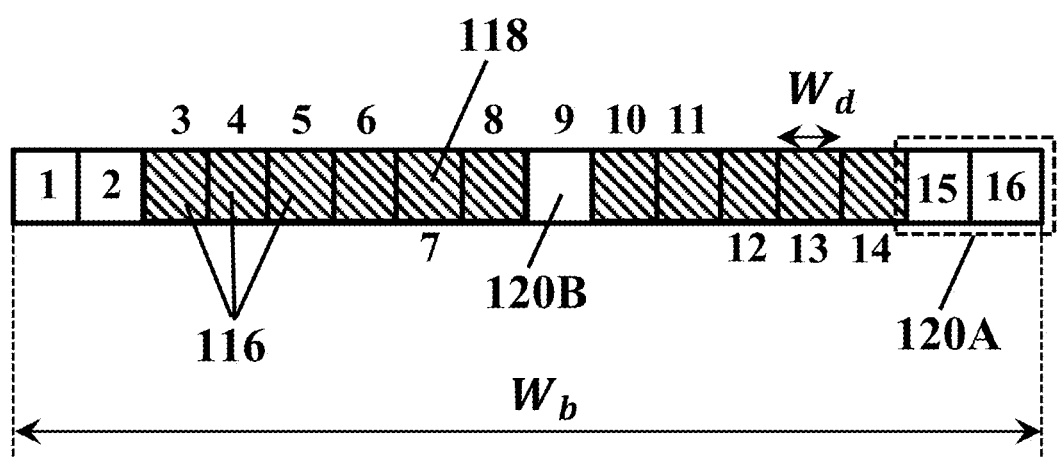
FIG. 1D shows a schematic of a row, consistent with one or more exemplary embodiments of the present disclosure.

FIG. 1D shows a schematic of a row, consistent with one or more exemplary embodiments of the present disclosure. An exemplary row 114 of the plurality of rows may include a plurality of actual detectors 116 (represented by three exemplary actual detectors in FIG. 1D) and an unused area. In an exemplary embodiment, the unused area may include a respective region in row 114 that may exclude the plurality of actual detectors. An exemplary actual detector 118 may include a scintillator that may be configured to detect an emission of a light photon when a photon passes through the scintillator. In an exemplary embodiment, an unused area may include a primary unused area 120A in which no actual detector exists (for example, a gap between actual detectors), or a secondary unused area 120B in which an actual detector may exist but is not functional, i.e., an existing actual detector may not be able to detect photon emissions. In an exemplary embodiment, secondary unused area 120B may include a broken or a degraded detector that may not accurately detect photon emissions.

Figure 2A:
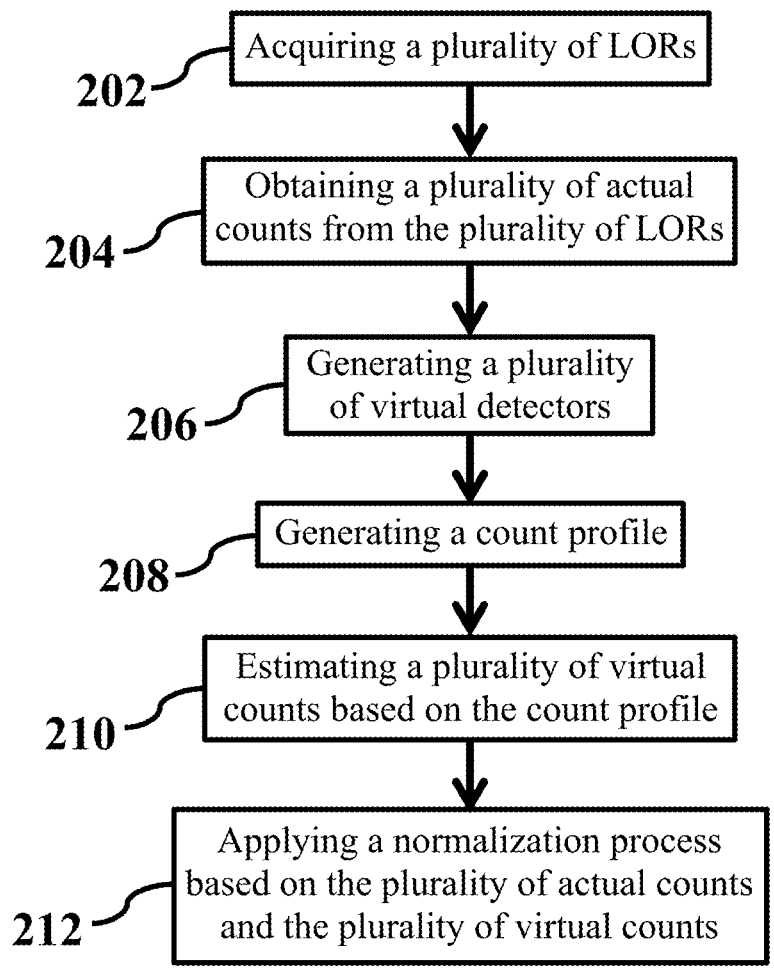
FIG. 2A shows a flowchart of a method for normalization of a PET scanner, consistent with one or more exemplary embodiments of the present disclosure.

FIG. 2A shows a flowchart of a method for normalization of a PET scanner, consistent with one or more exemplary embodiments of the present disclosure. An exemplary method 200 may be implemented utilizing different components of PET scanner 100. In an exemplary embodiment, method 200 may include acquiring a plurality of lines of response (LORs) by scanning a normalization phantom (step 202), obtaining a plurality of actual counts from the plurality of LORs (step 204), generating a plurality of virtual detectors in each of the plurality of rows by assigning the unused area to the plurality of virtual detectors (step 206), generating a count profile for plurality of actual detectors 116 (step 208), estimating a plurality of virtual counts based on the count profile (step 210), and applying a normalization process on plurality of blocks 106 based on the plurality of actual counts and the plurality of virtual counts (step 212).

Referring again to FIG. 1A, in an exemplary embodiment, step 202 may include acquiring a plurality of LORs by scanning a normalization phantom 120. In an exemplary embodiment, scanning may include exposing normalization phantom 120 to PET scanner 100 by placing normalization phantom 120 inside plurality of block rings 102. In an exemplary embodiment, normalization phantom 120 may include a homogenous cylindrical phantom.

Referring again to FIGS. 1B and 1D, an exemplary LOR 122 of the plurality of LORs may be generated after an annihilation photon 124 is created from a positron that may be radiated from normalization phantom 120. In an exemplary embodiment, LOR 122 may include a pair of light beams that may be received at a pair of blocks of plurality of blocks 106 by a respective actual detector at each block. Therefore, in an exemplary embodiment, LOR 122 may be associated with actual detector 118. In an exemplary embodiment, LOR 122 may be detected by actual detector 118.

Figure 2B:
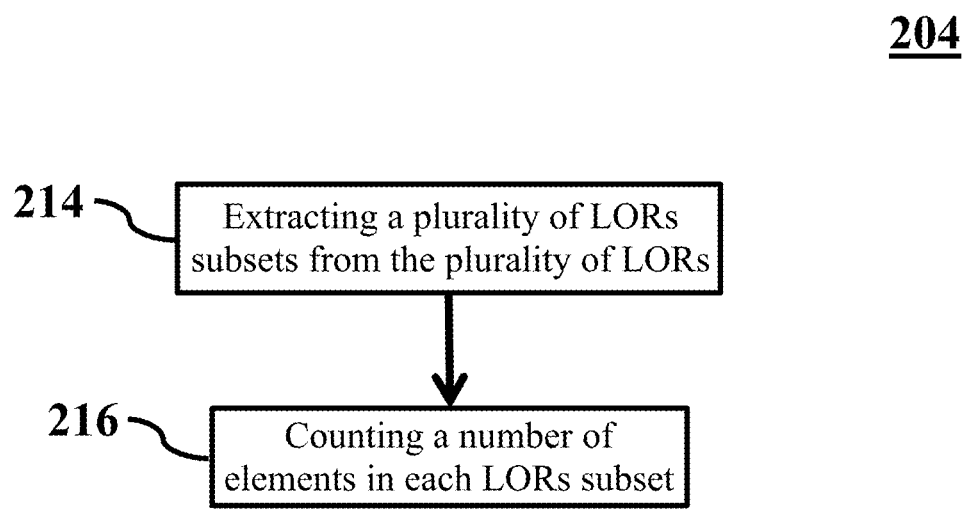
FIG. 2B shows a flowchart for obtaining a plurality of actual counts from a plurality of lines of response (LORs), consistent with one or more exemplary embodiments of the present disclosure.

For further detail with regards to step 204, FIG. 2B shows a flowchart for obtaining a plurality of actual counts from a plurality of LORs, consistent with one or more exemplary embodiments of the present disclosure. In an exemplary embodiment, step 204 may include extracting a plurality of LORs subsets from the plurality of LORs (step 214) and counting a number of elements in each LORs subset of the plurality of LORs subsets (step 216).

In further detail with respect to step 214, in an exemplary embodiment, each of the plurality of LORs subsets may be associated with a respective actual detector of the plurality of actual detectors. Referring again to FIG. 1D, extracting an exemplary LORs subset may include detecting a number of LORs by actual detector 118. In an exemplary embodiment, every actual detector in row 114 may detect a respective number of LORs by generating a burst of light each time a photon reaches a scintillator on an actual detector. Therefore, in an exemplary embodiment, each of the plurality of LORs subsets may include a respective number of LORs that may be detected by each respective actual detector in row 114. In an exemplary embodiment, each detected LOR may be converted to an electrical signal by a photomultiplier that may be coupled to a respective actual detector. Consequently, the electrical signal may be sent to an exemplary processor that may be configured to count a number of electrical signals generated by a respective actual detector. As a result, the number of elements in each LORs subset may be obtained by counting the number of respective electrical signals associated with a respective actual detector. In an exemplary embodiment, by counting the number of elements in each LORs subset (step 216) a respective actual count may be obtained that is associated with a respective actual detector.

Figure 2C:
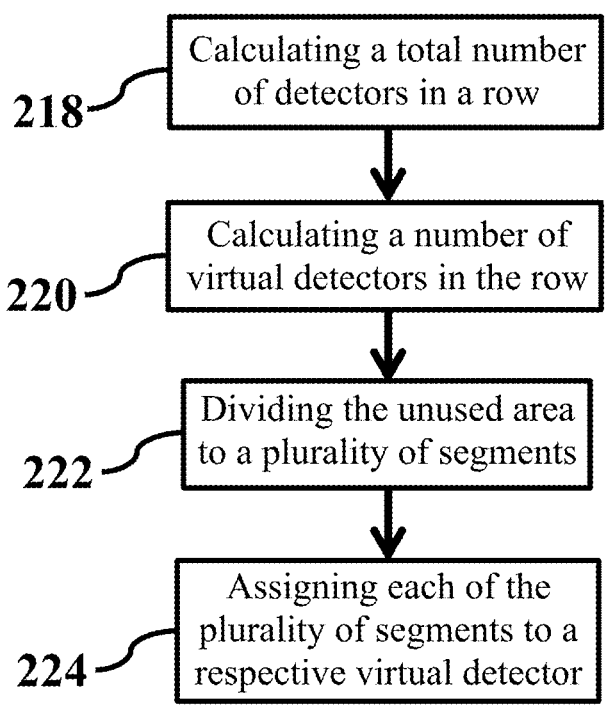
FIG. 2C shows a flowchart for assigning an unused area to a plurality of virtual detectors, consistent with one or more exemplary embodiments of the present disclosure.

For further detail regarding step 206, FIG. 2C shows a flowchart for assigning an unused area to a plurality of virtual detectors, consistent with one or more exemplary embodiments of the present disclosure. In an exemplary embodiment, assigning the unused area to the plurality of virtual detectors may include calculating a total number of detectors in a row of the plurality of rows (step 218), calculating a number of virtual detectors in the row (step 220), dividing the unused area to a plurality of segments (step 222), and assigning each of the plurality of segments to a respective virtual detector of the plurality of virtual detectors (step 224).

Referring again to FIG. 1D, in an exemplary embodiment, step 218 may include calculating a total number of detectors in row 114 according to an operation defined by the following:

$$N_{opt} = \text{round}\left(\frac{W_b}{W_d}\right) \qquad \text{Equation (1)}$$

where:
$N_{opt}$ is the total number of detectors in row 114,
$W_b$ is a width of block 108, and
$W_d$ is a width of each of plurality of actual detectors 116.

Referring again to FIGS. 1A and 1C, in an exemplary embodiment, $W_b$ may refer to an axial width 126 of block 108 that may be parallel to axial direction 103. In an exemplary embodiment, $W_b$ may refer to a transaxial width 128 of block 108 that may be perpendicular to axial direction 103. In an exemplary embodiment, Equation (1) may provide a maximum number of detectors that may be placed in row 114, assuming a fixed and equal width $W_d$ for each of the detectors.

Referring again to FIG. 1B-1C, in an exemplary embodiment, for a polyhedral block ring similar to block ring 104, a transaxial width of block 108 may be calculated according to an operation defined by the following:

$$W_b = 2r\tan\frac{\pi}{N_b} \qquad \text{Equation (2)}$$

where r is an apothem of a polygonal face of a polyhedron and $N_b$ is a number of plurality of blocks 106. An exemplary polygonal face may include block 108.

Referring again to FIG. 1D, in an exemplary embodiment, step 220 may include calculating a number of virtual detectors in row 114 according to an operation defined by the following:

$$N_v = N_{opt} - N_a \qquad \text{Equation (3)}$$

where:
$N_v$ is the number the plurality of virtual detectors, and
$N_a$ is the number of the plurality of actual detectors.

In further detail with regards to step 222, in an exemplary embodiment, dividing the unused area to the plurality of segments may include dividing a width of the unused area to a predefined number. An exemplary predefined number may be equal to width $W_d$ of each of plurality of actual detectors 116. Next, in an exemplary embodiment, each separate portion of the unused area with a width of $W_d$ may be assigned to a respective segment of the plurality of segments. An exemplary plurality of segments are represented in FIG. 1D by unfilled squares. In an exemplary embodiment, a width of each segment of the plurality of segments may be equal to width $W_d$ of each of plurality of actual detectors 116.

For further detail with respect to step 224, in an exemplary embodiment, assigning each of the plurality of segments to a respective virtual detector may include assigning a separate index to each of the plurality of segments based on a position of each segment. In an exemplary embodiment, each index may correspond to a respective virtual detector. Exemplary plurality of segments are shown in FIG. 1D that are indexed by 1, 2, 9, 15 and 16. In an exemplary embodiment, indexing each segment may be consistent with a position of the segment. In an exemplary embodiment, each segment of the plurality of segments may be considered a virtual detector. Therefore, in an exemplary embodiment, a number of the plurality of segments may be equal to the number of the plurality of virtual detectors.

Referring again to FIG. 2A, in an exemplary embodiment, step 208 may include generating the count profile by fitting a curve to variations of the plurality of actual counts with respect to a plurality of actual positions. In an exemplary embodiment, each of the plurality of actual positions may be associated with a respective actual detector of the plurality of actual detectors.

Figure 3:
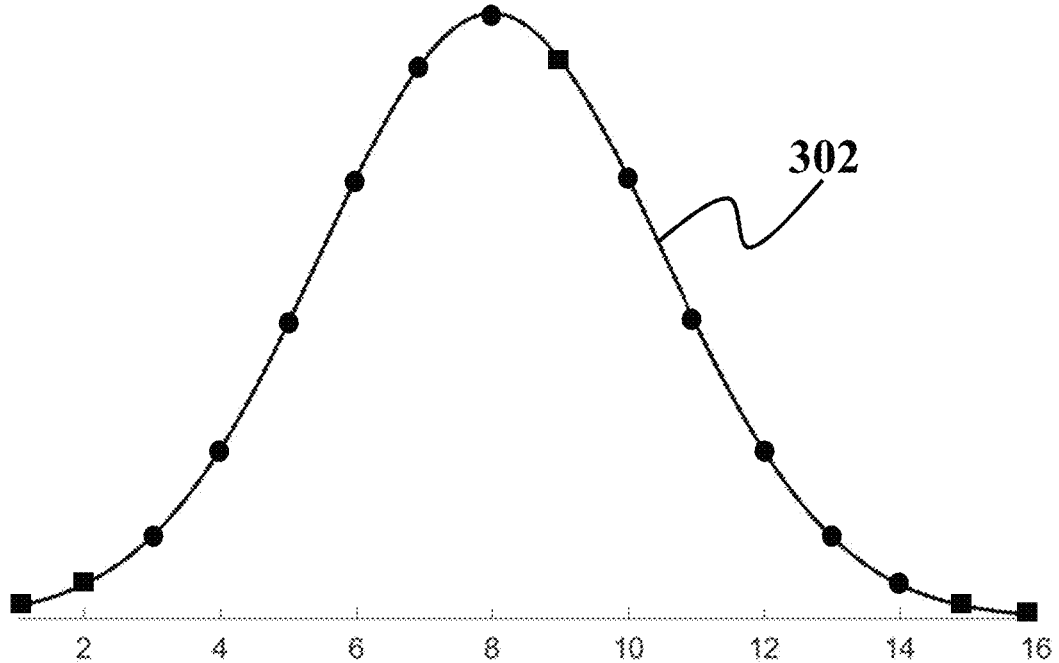
FIG. 3 shows a count profile, consistent with one or more exemplary embodiments of the present disclosure.

In further detail regarding step 208, FIG. 3 shows a count profile, consistent with one or more exemplary embodiments of the present disclosure. An exemplary count profile 300 may be associated with the plurality of actual counts. In an exemplary embodiment, count profile 300 may include variations of the plurality of actual counts with respect to the plurality of actual positions.

Referring again to FIG. 1D, in an exemplary embodiment, the plurality of actual positions may include positions 3-8 and 10-14. In an exemplary embodiment, each of the plurality of actual positions may correspond a respective actual detector of plurality of actual detectors 116. Exemplary actual counts corresponding to each of the plurality of actual positions are represented by circular marks on count profile 300. In an exemplary embodiment, a curve 302 may be fit to variations of the plurality of actual counts to generate count profile 300. In an exemplary embodiment, different curve fitting methods may be utilized to construct curve 302. An exemplary curve fitting approach may include obtaining a polynomial model for variations of the plurality of actual counts with respect to the plurality of actual positions utilizing a polynomial regression analysis. An exemplary polynomial model may estimate each of the plurality of actual counts at each respective position with a minimized estimation error.

For further detail with respect to step 210, in an exemplary embodiment, estimating the plurality of virtual counts may include estimating each of the plurality of virtual counts by extracting a respective value from curve 302. In an exemplary embodiment, extracting each value from curve 302 may include reading an amplitude of curve 302 at a respective position. An exemplary respective value may correspond to a respective virtual position of a plurality of virtual positions. In an exemplary embodiment, the plurality of virtual positions may include positions 1-2, 9, and 15-16. In an exemplary embodiment, each of the plurality of virtual positions may be associated with a respective virtual detector of the plurality of virtual detectors. Exemplary virtual counts corresponding to each of the plurality of virtual positions are represented by square marks on count profile 300.

Figure 2D:
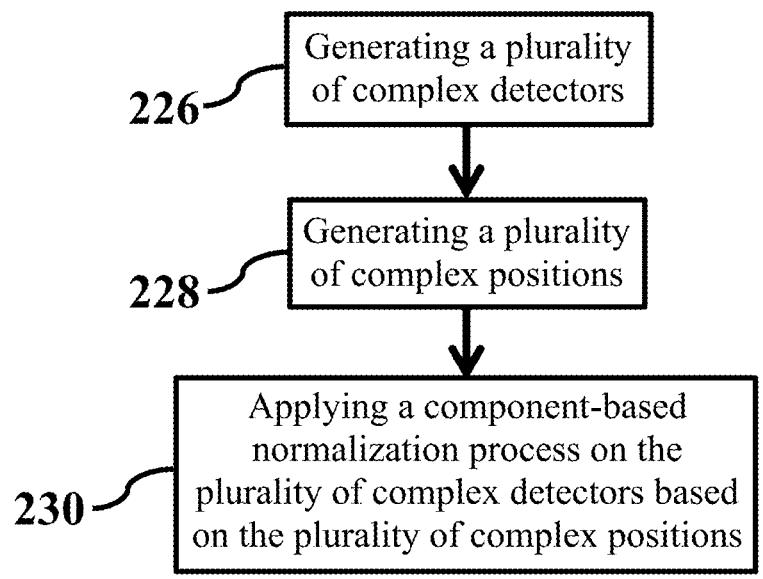
FIG. 2D shows a flowchart for applying a normalization process, consistent with one or more exemplary embodiments of the present disclosure.

In further detail with regards to step 210, FIG. 2D shows a flowchart for applying a normalization process, consistent with one or more exemplary embodiments of the present disclosure. In an exemplary embodiment, applying the normalization process may include generating a plurality of complex detectors by integrating the plurality of actual detectors and the plurality of virtual detectors (step 226), generating a plurality of complex positions by integrating the plurality of actual positions and the plurality of virtual positions (step 228), and applying a normalization process on the plurality of complex detectors based on the plurality of complex positions (step 230).

Referring again to FIG. 1D, in an exemplary embodiment, integrating the plurality of actual detectors and the plurality of virtual detectors in step 226 may include generating a set of complex detectors that may include the plurality of actual detectors and the plurality of virtual detectors. In other words, in an exemplary embodiment, each of the plurality of actual detectors and the plurality of virtual detectors may be labelled as a respective complex detector of a plurality of complex detectors. Therefore, an exemplary plurality of complex detectors may include each of plurality of actual detectors 116 and each of the plurality of virtual detectors. As a result, in an exemplary embodiment, each of the plurality of complex detectors may be associated with a respective complex count of a plurality of complex counts. In an exemplary embodiment, the respective complex count may include a respective actual count of the plurality of actual counts or a respective virtual count of the plurality of virtual counts.

For further detail regarding step 228, in an exemplary embodiment, integrating the plurality of actual positions and the plurality of virtual positions may include generating a set of complex positions that may include the plurality of actual positions and the plurality of virtual positions. In other words, in an exemplary embodiment, each of the plurality of actual positions and the plurality of virtual positions may be labelled as a respective complex position of a plurality of complex positions. As a result, in an exemplary embodiment, the plurality of complex positions may include each of the plurality of actual positions and each of the plurality of virtual positions. Therefore, an exemplary plurality of complex positions may include positions 1-16 in row 114. In an exemplary embodiment, each of the plurality of complex positions may be associated with a respective complex detector of the plurality of complex detectors.

In further detail regarding step 230, in an exemplary embodiment, different normalization processes may be applied on the plurality of complex detectors based on a respective complex count and a respective complex position of each of the plurality of complex detectors. An exemplary normalization process may include a component-based normalization process. In an exemplary embodiment, the component-based normalization process may include dividing normalization components into separate terms (including detector efficiency, block profile factors, geometrical parameters, time and spatial misalignments) and individually compensating each term. In an exemplary embodiment, a compensation process may be applied on each complex detector by locating each complex detector utilizing a respective complex position and calculating respective normalization components based on a respective complex count.

Figure 4:
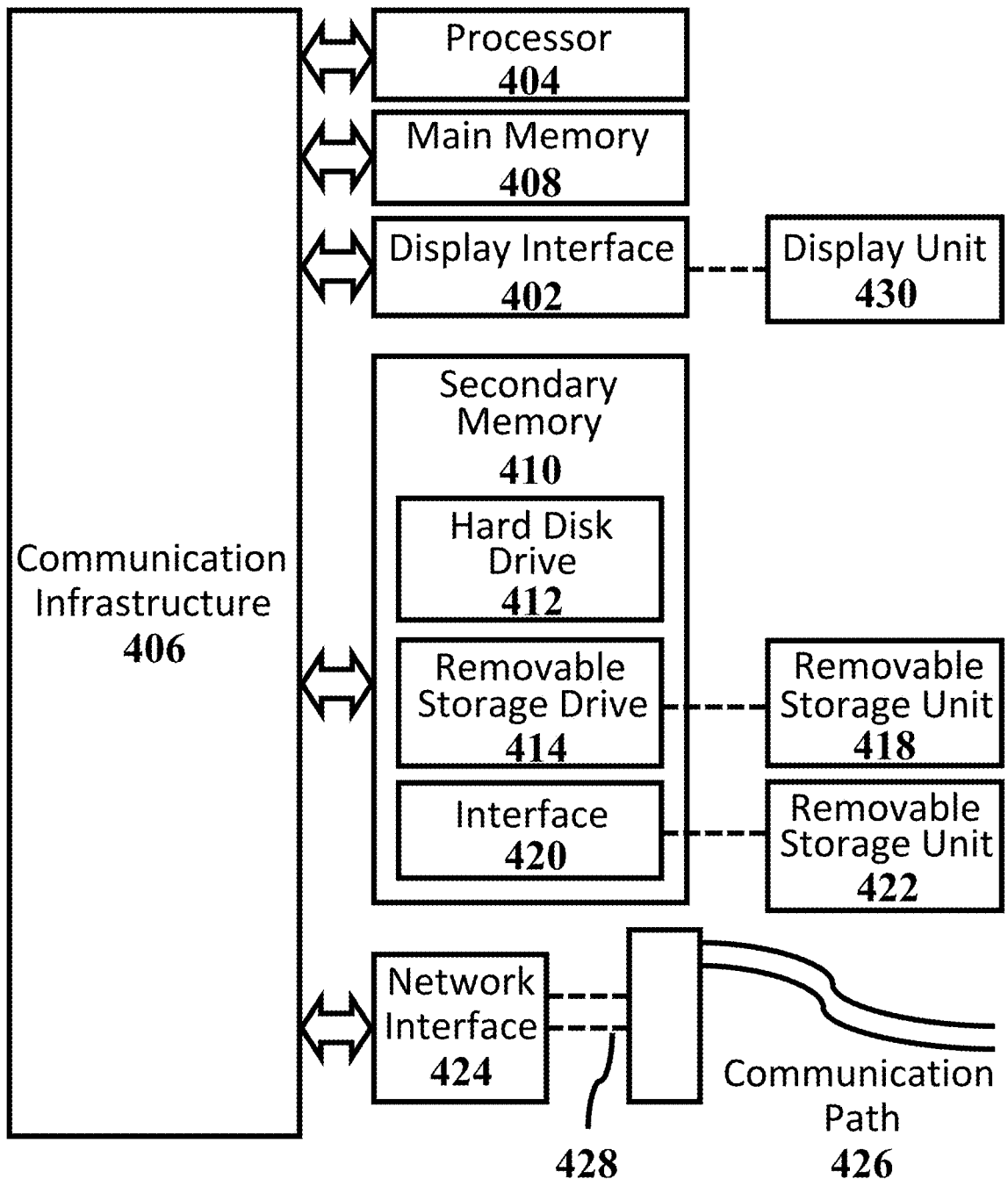
FIG. 4 shows a high-level functional block diagram of a computer system, consistent with one or more exemplary embodiments of the present disclosure.

FIG. 4 shows an example computer system 400 in which an embodiment of the present invention, or portions thereof, may be implemented as computer-readable code, consistent with exemplary embodiments of the present disclosure. For example, steps 204-212 of method 200 and detailed steps 214-230 provided in steps 204, 206, and 210 may be implemented in computer system 400 using hardware, software, firmware, tangible computer readable media having instructions stored thereon, or a combination thereof and may be implemented in one or more computer systems or other processing systems. Hardware, software, or any combination of such may embody any of the modules and components in FIGS. 1A-D and 2A-2D.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 400. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 404 may be a special purpose or a general-purpose processor device. As will be appreciated by persons skilled in the relevant art, processor device 404 may also be a single processor in a multi-core/multiprocessor system, such system operating alone, or in a cluster of computing devices operating in a cluster or server farm. Processor device 404 may be connected to a communication infrastructure 406, for example, a bus, message queue, network, or multi-core message-passing scheme.

In an exemplary embodiment, computer system 400 may include a display interface 402, for example a video connector, to transfer data to a display unit 430, for example, a monitor. Computer system 400 may also include a main memory 408, for example, random access memory (RAM), and may also include a secondary memory 410. Secondary memory 410 may include, for example, a hard disk drive 412, and a removable storage drive 414. Removable storage drive 414 may include a floppy disk drive, a magnetic tape drive, an optical disk drive, a flash memory, or the like. Removable storage drive 414 may read from and/or write to a removable storage unit 418 in a well-known manner. Removable storage unit 418 may include a floppy disk, a magnetic tape, an optical disk, etc., which may be read by and written to by removable storage drive 414. As will be appreciated by persons skilled in the relevant art, removable storage unit 418 may include a computer usable storage medium having stored therein computer software and/or data.

In alternative implementations, secondary memory 410 may include other similar means for allowing computer programs or other instructions to be loaded into computer system 400. Such means may include, for example, a removable storage unit 422 and an interface 420. Examples of such means may include a program cartridge and cartridge interface (such as that found in video game devices), a removable memory chip (such as an EPROM, or PROM) and associated socket, and other removable storage units 422 and interfaces 420 which allow software and data to be transferred from removable storage unit 422 to computer system 400.

Computer system 400 may also include a communications interface 424. Communications interface 424 allows software and data to be transferred between computer system 400 and external devices. Communications interface 424 may include a modem, a network interface (such as an Ethernet card), a communications port, a PCMCIA slot and card, or the like. Software and data transferred via communications interface 424 may be in the form of signals, which may be electronic, electromagnetic, optical, or other signals capable of being received by communications interface 424. These signals may be provided to communications interface 424 via a communications path 426. Communications path 426 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 418, removable storage unit 422, and a hard disk installed in hard disk drive 412. Computer program medium and computer usable medium may also refer to memories, such as main memory 408 and secondary memory 410, which may be memory semiconductors (e.g. DRAMs, etc.).

Computer programs (also called computer control logic) are stored in main memory 508 and/or secondary memory 410. Computer programs may also be received via communications interface 424. Such computer programs, when executed, enable computer system 400 to implement different embodiments of the present disclosure as discussed herein. In particular, the computer programs, when executed, enable processor device 404 to implement the processes of the present disclosure, such as the operations in method 200 illustrated by flowchart 200 of FIG. 2A, flowchart 204 of FIG. 2B, flowchart 206 of FIG. 2C, and flowchart 210 of FIG. 2D discussed above. Accordingly, such computer programs represent controllers of computer system 400. Where an exemplary embodiment of method 200 is implemented using software, the software may be stored in a computer program product and loaded into computer system 400 using removable storage drive 414, interface 420, and hard disk drive 412, or communications interface 424.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

EXAMPLE

In this example, an impact of adding virtual detectors to a PET scanner on imaging quality is demonstrated. An exemplary implementation of method 200 is implemented on a dedicated small animal PET imaging system, consisting of ten (24×24 LYSO: Ce) blocks coupled to a 12×12 Silicon Photomultipliers (SiPMs) array. The scanner has 24 detector rings (i.e., transaxial rows at each block ring) and 240 LYSO (2×2×10 mm$^3$) detectors per ring (i.e., all detectors in same transaxial rows of all blocks in a single block ring). The ring diameter, effective transaxial and axial field of views (FOV) are 166 mm, 100 mm, and 50.4 mm, respectively.

A cylindrical normalization phantom with a 9.5 cm inner diameter and a 6 cm height is filled with 75 Mbq $^{18}$F solution, positioned at the center of the FOV and scanned for 20 hours. More than 10$^9$ LOR events are collected.

Figure 5A:
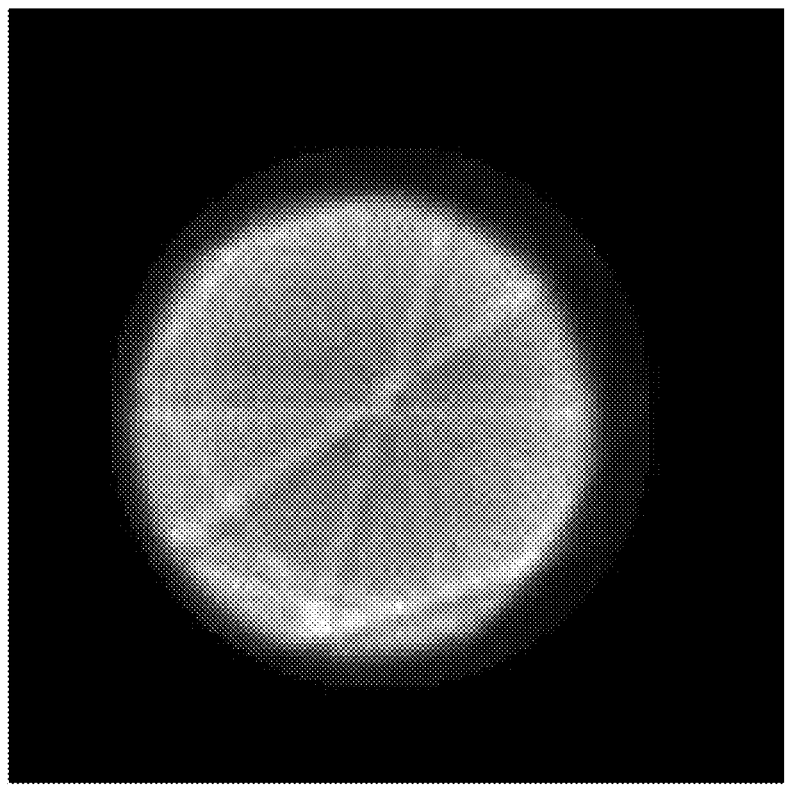
FIG. 5A shows a transverse PET image of a homogenous cylindrical phantom prior to adding virtual detectors to a PET scanner, consistent with one or more exemplary embodiments of the present disclosure.

FIG. 5A shows a transverse PET image of a homogenous cylindrical phantom prior to adding virtual detectors to a PET scanner, consistent with one or more exemplary embodiments of the present disclosure. Several nonuniform areas are observed in the image of FIG. 5A due to gap regions between detector modules.

Figure 5B:
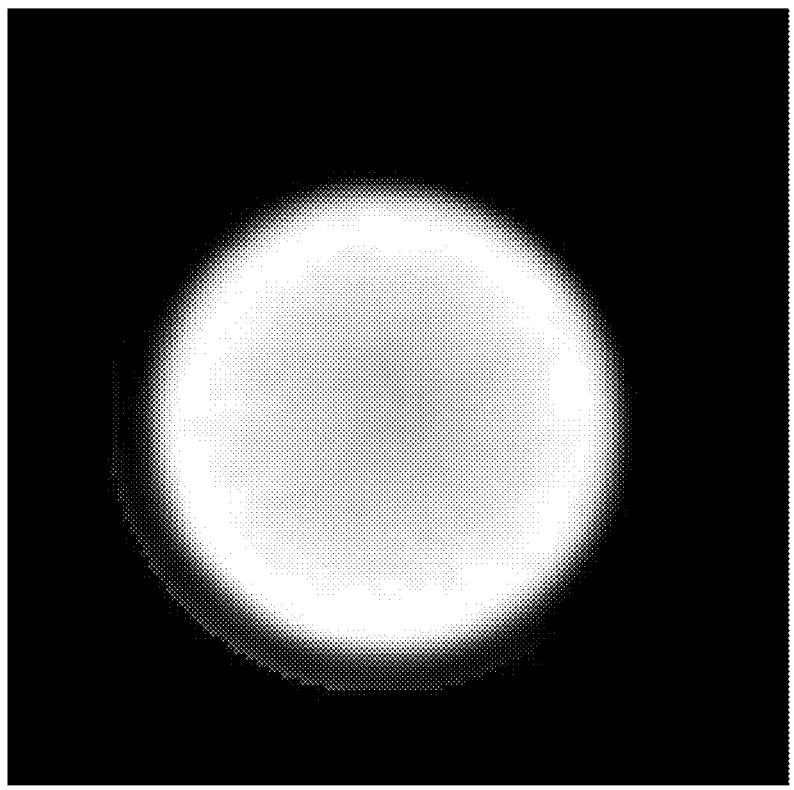
FIG. 5B shows a transverse PET image of a homogenous cylindrical phantom after adding virtual detectors to a PET scanner, consistent with one or more exemplary embodiments of the present disclosure.

FIG. 5B shows a transverse PET image of a homogenous cylindrical phantom after implementing a component-based normalization technique, consistent with one or more exemplary embodiments of the present disclosure. The addition of virtual detectors and removal of gap regions shows a pronounced improvement on uniformity index and image noise.

Figure 6:
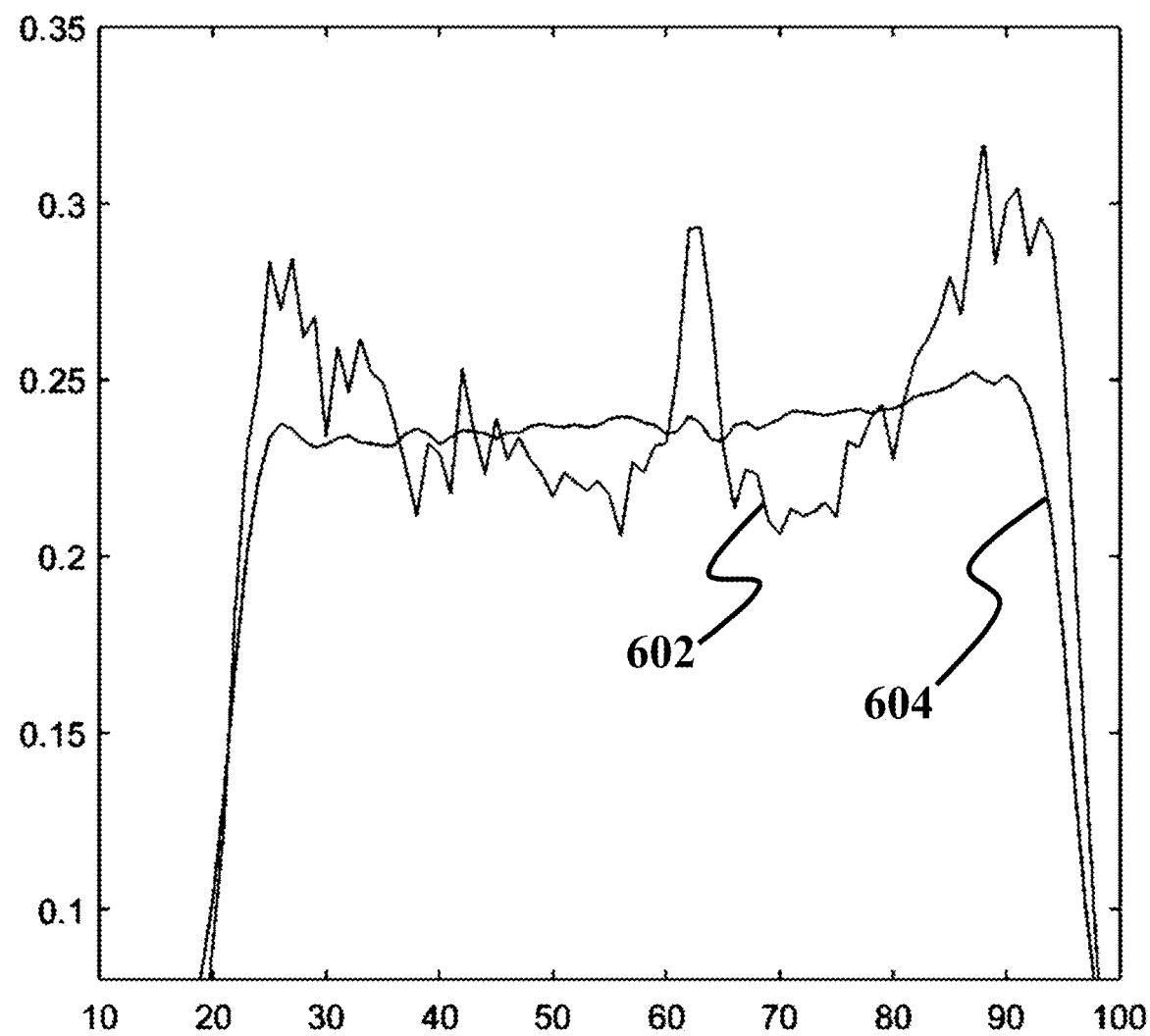
FIG. 6 shows central profiles of a homogeneous cylindrical phantom with and without normalization, consistent with one or more exemplary embodiments of the present disclosure.

FIG. 6 shows central profiles of a homogeneous cylindrical phantom with and without normalization, consistent with one or more exemplary embodiments of the present disclosure. A central profile 602 is obtained without applying normalization on PET detectors and a central profile 604 is obtained after applying a component-based normalization method. As shown in FIG. 6, noise level and non-uniformity of profile 602 are significantly higher than noise level and non-uniformity of profile 604.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for normalization of a positron emission tomography (PET) scanner comprising a plurality of blocks, each of the plurality of blocks comprising a plurality of rows, each of the plurality of rows comprising a plurality of actual detectors and an unused area comprising a respective region in each of the plurality of rows, the respective region excluding the plurality of actual detectors, the method comprising:
   acquiring a plurality of lines of response (LORs) by scanning a normalization phantom utilizing the PET scanner, each respective LOR of the plurality of LORs associated with an actual detector of the plurality of actual detectors;
   obtaining, utilizing one or more processors, a plurality of actual counts by:
      extracting a plurality of LORs subsets from the plurality of LORs, each of the plurality of LORs subsets associated with a respective actual detector of the plurality of actual detectors; and
      counting a number of elements in each LORs subset of the plurality of LORs sub sets;
   generating, utilizing the one or more processors, a plurality of virtual detectors in each of the plurality of rows by assigning the unused area to the plurality of virtual detectors;
   generating, utilizing the one or more processors, a count profile for the plurality of actual detectors, the count profile associated with the plurality of actual counts;
   estimating, utilizing the one or more processors, a plurality of virtual counts associated with the plurality of virtual detectors based on the count profile; and
   applying, utilizing the one or more processors, a normalization process on the plurality of blocks based on the plurality of actual counts and the plurality of virtual counts.

2. The method of claim 1, wherein assigning the unused area to the plurality of virtual detectors comprises:
   calculating a total number of detectors in a row of the plurality of rows according to an operation defined by the following:

$$N_{opt} = \text{round}\left(\frac{W_b}{W_d}\right)$$

where:
      $N_{opt}$ is the total number of detectors in the row,
      $W_b$ is a width of the block, and
      $W_d$ is a width of each of the plurality of actual detectors;
   calculating a number of virtual detectors in the row according to an operation defined by the following:

$N_v = N_{opt} - N_a$ where:
      $N_v$ is the number the plurality of virtual detectors, and
      $N_a$ is the number of the plurality of actual detectors;
   dividing the unused area to a plurality of segments, a number of the plurality of segments equal to the number of the plurality of virtual detectors; and
   assigning each of the plurality of segments to a respective virtual detector of the plurality of virtual detectors.

3. The method of claim 2, wherein calculating the total number of detectors comprises calculating the width of the block according to an operation defined by the following:

$$W_b = 2r\tan\frac{\pi}{N_b}$$

where:
      r is an apothem of a polygonal face of a polyhedron, the polygonal face comprising the block, and
      $N_b$ is a number of the plurality of the blocks.

4. The method of claim 1, wherein generating the count profile comprises fitting a curve to variations of the plurality of actual counts with respect to a plurality of actual positions, each of the plurality of actual positions associated with a respective actual detector of the plurality of actual detectors.

5. The method of claim 4, wherein estimating the plurality of virtual counts comprises estimating each of the plurality of virtual counts by extracting a respective value from the curve, the respective value corresponding to a respective virtual position of a plurality of virtual positions, each of the plurality of virtual positions associated with a respective virtual detector of the plurality of virtual detectors.

6. The method of claim 1, wherein applying the normalization process comprises:
   generating a plurality of complex detectors by integrating the plurality of actual detectors and the plurality of virtual detectors;
   generating a plurality of complex positions by integrating the plurality of actual positions and the plurality of virtual positions, each of the plurality of complex positions associated with a respective complex detector of the plurality of complex detectors; and
   applying a component-based normalization process on the plurality of complex detectors based on the plurality of complex positions.

7. The method of claim 1, wherein scanning the normalization phantom comprises scanning a homogenous cylindrical phantom.

8. A system for normalization of positron emission tomography (PET), the system comprising:
   a PET scanner comprising a plurality of blocks, each of the plurality of blocks comprising a plurality of rows, each of the plurality of rows comprising a plurality of actual detectors and an unused area comprising a respective region in each of the plurality of rows, the respective region excluding the plurality of actual detectors, the PET scanner configured to acquire a plurality of lines of response (LORs) by scanning a normalization phantom, each respective LOR of the plurality of LORs associated with an actual detector of the plurality of actual detectors;
   a memory having processor-readable instructions stored therein; and
   one or more processors configured to access the memory and execute the processor-readable instructions, which, when executed by the one or more processors configures the one or more processors to perform a method, the method comprising:
      obtaining a plurality of actual counts by:
         extracting a plurality of LORs subsets from the plurality of LORs, each of the plurality of LORs subsets associated with a respective actual detector of the plurality of actual detectors; and
counting a number of elements in each LORs subset of the plurality of LORs subsets;
generating a plurality of virtual detectors in each of the plurality of rows by assigning the unused area to the plurality of virtual detectors;
fitting a curve to variations of the plurality of actual counts with respect to a plurality of actual positions, each of the plurality of actual positions associated with a respective actual detector of the plurality of actual detectors;
estimating a plurality of virtual counts associated with the plurality of virtual detectors by extracting a plurality of values from the curve, each of the plurality of values corresponding to a respective virtual position of a plurality of virtual positions, each of the plurality of virtual positions associated with a respective virtual detector of the plurality of virtual detectors; and
applying a normalization process on the plurality of blocks based on the plurality of actual counts and the plurality of virtual counts.

9. The system of claim 8, wherein assigning the unused area to the plurality of virtual detectors comprises:
calculating a total number of detectors in a row of the plurality of rows according to an operation defined by the following:

$$N_{opt} = \text{round}\left(\frac{W_b}{W_d}\right)$$

where:
$N_{opt}$ is the total number of detectors in the row,
$W_b$ is a width of the block, and
$W_d$ is a width of each of the plurality of actual detectors;
calculating a number of virtual detectors in the row according to an operation defined by the following:

$$N_v = N_{opt} - N_a$$

where:
$N_v$ is the number the plurality of virtual detectors, and
$N_a$ is the number of the plurality of actual detectors;
dividing the unused area to a plurality of segments, a number of the plurality of segments equal to the number of the plurality of virtual detectors; and
assigning each of the plurality of segments to a respective virtual detector of the plurality of virtual detectors.

10. The system of claim 9, wherein calculating the total number of detectors comprises calculating the width of the block according to an operation defined by the following:

$$W_b = 2r\tan\frac{\pi}{N_b}$$

where:
r is an apothem of a polygonal face of a polyhedron, the polygonal face comprising the block, and
$N_b$ is a number of the plurality of the blocks.

11. The system of claim 8, wherein applying the normalization process comprises:

generating a plurality of complex detectors by integrating the plurality of actual detectors and the plurality of virtual detectors;
generating a plurality of complex positions by integrating the plurality of actual positions and the plurality of virtual positions, each of the plurality of complex positions associated with a respective complex detector of the plurality of complex detectors; and
applying a component-based normalization process on the plurality of complex detectors based on the plurality of complex positions.

12. The system of claim 8, wherein the normalization phantom comprises a homogenous cylindrical phantom.

13. A positron emission tomography (PET) system, comprising:
a plurality of blocks, each of the plurality of blocks comprising a plurality of rows, each of the plurality of rows comprising a plurality of actual detectors and an unused area comprising a respective region in each of the plurality of rows, the respective region excluding the plurality of actual detectors, each of the plurality of actual detectors configured to acquire a respective line of response (LOR) of a plurality of LORs by scanning a normalization phantom;
a memory having processor-readable instructions stored therein; and
one or more processors configured to access the memory and execute the processor-readable instructions, which, when executed by the one or more processors configures the one or more processors to perform a method, the method comprising:
obtaining a plurality of actual counts by:
extracting a plurality of LORs subsets from the plurality of LORs, each of the plurality of LORs subsets associated with a respective actual detector of the plurality of actual detectors; and
counting a number of elements in each LORs subset of the plurality of LORs subsets;
generating a plurality of virtual detectors in each of the plurality of rows by assigning the unused area to the plurality of virtual detectors;
generating a count profile for the plurality of actual detectors, the count profile associated with the plurality of actual counts;
estimating a plurality of virtual counts associated with the plurality of virtual detectors based on the count profile; and
applying a normalization process on the plurality of blocks based on the plurality of actual counts and the plurality of virtual counts.

14. The system of claim 13, wherein assigning the unused area to the plurality of virtual detectors comprises:
calculating a total number of detectors in a row of the plurality of rows according to an operation defined by the following:

$$N_{opt} = \text{round}\left(\frac{W_b}{W_d}\right)$$

where:
$N_{opt}$ is the total number of detectors in the row,
$W_b$ is a width of the block, and
$W_d$ is a width of each of the plurality of actual detectors;

calculating a number of virtual detectors in the row according to an operation defined by the following:

$$N_v = N_{opt} - N_a$$

where:
- $N_v$ is the number the plurality of virtual detectors, and
- $N_a$ is the number of the plurality of actual detectors;

dividing the unused area to a plurality of segments, a number of the plurality of segments equal to the number of the plurality of virtual detectors; and assigning each of the plurality of segments to a respective virtual detector of the plurality of virtual detectors.

15. The system of claim 14, wherein calculating the total number of detectors comprises calculating the width of the block according to an operation defined by the following:

$$W_b = 2r\tan\frac{\pi}{N_b}$$

where:
- r is an apothem of a polygonal face of a polyhedron, the polygonal face comprising the block, and
- $N_b$ is a number of the plurality of the blocks.

16. The system of claim 13, wherein generating the count profile comprises fitting a curve to variations of the plurality of actual counts with respect to a plurality of actual positions, each of the plurality of actual positions associated with a respective actual detector of the plurality of actual detectors.

17. The system of claim 16, wherein estimating the plurality of virtual counts comprises estimating each of the plurality of virtual counts by extracting a respective value from the curve, the respective value corresponding to a respective virtual position of a plurality of virtual positions, each of the plurality of virtual positions associated with a respective virtual detector of the plurality of virtual detectors.

18. The system of claim 13, wherein applying the normalization process comprises:

generating a plurality of complex detectors by integrating the plurality of actual detectors and the plurality of virtual detectors;

generating a plurality of complex positions by integrating the plurality of actual positions and the plurality of virtual positions, each of the plurality of complex positions associated with a respective complex detector of the plurality of complex detectors; and applying a component-based normalization process on the plurality of complex detectors based on the plurality of complex positions.

19. The system of claim 13, wherein the normalization phantom comprises a homogenous cylindrical phantom.

* * * * *